(12) United States Patent
Parker

(10) Patent No.: US 6,684,091 B2
(45) Date of Patent: *Jan. 27, 2004

(54) REUSABLE PULSE OXIMETER PROBE AND DISPOSABLE BANDAGE METHOD

(75) Inventor: Brent Parker, Murrieta, CA (US)

(73) Assignee: Sensidyne, Inc., Clearwater, FL (US)

(*) Notice: Subject to any disclaimer, the term of this patent is extended or adjusted under 35 U.S.C. 154(b) by 109 days.

This patent is subject to a terminal disclaimer.

(21) Appl. No.: 09/758,038

(22) Filed: Jan. 11, 2001

(65) Prior Publication Data

US 2001/0029325 A1 Oct. 11, 2001

Related U.S. Application Data

(63) Continuation-in-part of application No. 09/417,898, filed on Oct. 14, 1999, now Pat. No. 6,343,224, which is a continuation-in-part of application No. 09/289,647, filed on Apr. 12, 1999, now Pat. No. 6,144,868.
(60) Provisional application No. 60/104,332, filed on Oct. 15, 1998.

(51) Int. Cl.⁷ ............................................. A61B 5/00
(52) U.S. Cl. ........................................ 600/344; 600/310
(58) Field of Search ........................... 600/310, 322, 600/323, 340, 344, 473, 476

(56) References Cited

U.S. PATENT DOCUMENTS

| | | |
|---|---|---|
| 4,621,643 A | 11/1986 | New, Jr. et al. |
| 4,685,464 A | 8/1987 | Goldberger et al. |
| 4,700,708 A | 10/1987 | New, Jr. et al. |
| 4,830,014 A | 5/1989 | Goodman et al. |
| 5,090,410 A | 2/1992 | Saper et al. |
| 5,094,240 A | 3/1992 | Muz |
| 5,170,786 A | 12/1992 | Thomas et al. |
| 5,387,122 A | 2/1995 | Goldberger et al. ......... 439/353 |
| 5,437,275 A * | 8/1995 | Amundsen et al. ......... 600/323 |
| 5,507,286 A | 4/1996 | Solenberger |
| 5,664,270 A | 9/1997 | Bell et al. ....................... 5/600 |
| 5,673,693 A | 10/1997 | Solenberger |
| 5,678,544 A | 10/1997 | DeLonzor et al. |
| 5,817,010 A | 10/1998 | Hibl ........................... 600/344 |
| RE36,000 E | 12/1998 | Swedlow et al. |
| 5,879,373 A | 3/1999 | Röper et al. ................ 606/344 |
| 5,910,108 A | 6/1999 | Solenberger ................ 600/310 |
| 5,991,648 A | 11/1999 | Levin ......................... 600/344 |
| 6,014,576 A * | 1/2000 | Raley ......................... 600/344 |
| 6,144,868 A * | 11/2000 | Parker ........................ 600/344 |
| 6,343,224 B1 * | 1/2002 | Parker ........................ 600/344 |
| 6,519,487 B1 * | 2/2003 | Parker ........................ 600/344 |

FOREIGN PATENT DOCUMENTS

| | | |
|---|---|---|
| WO | WO 0021433 A | 4/2000 |
| WO | WO 00/42911 A | 7/2000 |

* cited by examiner

*Primary Examiner*—Eric F. Winakur
(74) *Attorney, Agent, or Firm*—Jim Zegeer

(57) ABSTRACT

A method of facilitating the intra-departmental or inter-institutional transport of a patient or patients requiring the pulse oximeter monitoring, and wherein the pulse oximeters used for monitoring the patient may be of different manufacturers, comprising affixing to the patient a bandage apparatus having a modular emitter and detector receptacles incorporated thereon. Each different manufacturers' pulse oximeter probe is provided with modular housings adapted to matedly engage and/or disengage the receptacles of the disposable bandage apparatus, thus enabling the patient to be monitored by pulse oximeters of different manufacturers without changing the bandage apparatus.

3 Claims, 9 Drawing Sheets

REUSABLE PULSE OXIMETER PROBE AND DISPOSABLE BANDAGE METHOD

REFERENCE TO RELATED APPLICATIONS

This application is a continuation-in-part application of my copending application Ser. No. 09/417,898, filed Oct. 14, 1999 entitled REUSABLE PULSE OXIMETER PROBE AND DISPOSABLE BANDAGE APPARATUS, now U.S. Pat. No. 6,343,224, which is a continuation-in-part of patent application Ser. No. 09/289,647 filed Apr. 12, 1999 and entitled REUSABLE PULSE OXIMETER PROBE AND DISPOSABLE BANDAGE APPARATUS, now U.S. Pat. No. 6,144,868 which in turn is a nonprovisional application based on provisional application serial No. 60/104,332 filed Oct. 15, 1998.

BACKGROUND OF THE INVENTION

Heretofore the use of pulse oximeter probes has been limited to the use of a costly reusable probe, which is contaminated by use on a patient, or cheaper, single-use probes, which, in the aggregate, amount to a considerable expenditure for a health care institution. The present invention relates to a method of making and affixing a reusable probe to a patient by means of disposable bandage apparatus so that there is no contact between the costly, reusable portion of the probe and the patient. The contaminated bandage apparatus, which is relatively inexpensive, can then be discarded after single patient use and the probe can be reused with a new bandage apparatus.

Others have attempted to convert single-use probes into multi-use probes through a lamination process. In that process, the original adhesive material is removed from the original manufacturer's sensor. The sensor is then laminated in a plastic sheath and the entire sheath is then inserted into a transparent, adhesive-backed sleeve, which is then adhered to a patient. After use, the probe can then be extracted from the sleeve and inserted into a new sleeve for use on another patient.

There are certain disadvantages to this method. Firstly, it is difficult to insert the flexible laminated sensor into a long sleeve. Secondly, the thickness of a laminated sensor inside of a sleeve makes it difficult to bend around, and to stick properly to, a human appendage. Thirdly, transmission and reception of infrared light can be affected by extraneous light entering from the sides of the sleeve. And, Fourthly, there is some dispute as to the affect on infrared light transmission when passing through the sleeve and the adhesive material coupled thereto.

One of the problems with pulse oximetry, and the continuity of monitoring a patient, is the vast array of different monitors used in different hospital departments. Many times a patient will start out in the emergency room (ER) where the hospital utilizes one particular brand of monitor. If a disposable probe is affixed to the patient, and the patient is then admitted to intensive care, the disposable probe that was affixed in the ER will only work if the pulse oximeter used in intensive care is of the same make as the one in the ER. If that same patient is once again taken to radiology, or to have an MRI done, once again these different departments may have different pulse oximeter monitors. What happens many times is that the disposable probes affixed in one department are thrown away and new ones are affixed in other departments. Obviously, this creates additional expense in providing pulse oximetry monitoring.

THE PRESENT INVENTION

The present invention not only solves the problems outlined above, but offers an alternative that is cheap to manufacture and easy to use.

Thus, the object of the present invention is to provide a method of facilitating the intra-departmental or inter-institutional transport of a patient or patients requiring the pulse oximeter monitoring, and wherein said pulse oximeters used for monitoring said patient may be of different manufacturers. The method comprises affixing to said patient a bandage apparatus having a modular emitter and detector receptacles incorporated thereon, providing each said different manufacturers' pulse oximeter probe with modular housings adapted to matedly engage and/or disengage with receptacles of the disposable bandage apparatus, thus enabling said patient to be monitored by pulse oximeters of different manufacturers without changing the affixed bandage apparatus.

With the present invention, intra-departmental or inter-institutional transport is greatly facilitated by having a bandage device which will accept probes of various manufacturers, as long as those probes contain housings that will matedly engage the receptacles of the disposable bandage apparatus.

Each reusable pulse oximeter probe has at least one light-emitting diode and one photocell detector wherein the emitter and detector are enclosed in plastic housings, one housing having an aperture or radiation transparent window aligned with the emitter, and the other housing having an aperture or radiation transparent window aligned with the detector. A disposable bandage apparatus which is a bandage strip having adhesive on at least a portion of at least one face thereof and at least two plastic receptacles mounted thereon, each receptacle having at least one aperture or radiation transparent window located therein. The probe housings can matedly engage the bandage receptacles and transmit and receive light through the apertures or radiation transparent windows of the mated housings and receptacles, and through the appendage of a patient. The apertures of the receptacles are large enough to accept the tubular protrusions of the housings for the purpose of concentric location and alignment of the housings to the receptacles and the proper transmission and reception of light therethrough. Sandwiched between the adhesive strip and the receptacles attached thereto, are translucent silicone windows or windows of another radiation transparent material for isolation of the reusable probe assembly from the patient. The bandage apparatus may be discarded after single patient use and the reusable probe may be used again on another patient in conjunction with another bandage apparatus. Additionally, the receptacles of the bandage apparatus may have a concave surface on one side thereof in order to seat conformably on a human digit, or they have a flat surface on at least one side thereof in order to attach conformably to a human foot, nose, or ear. The housings and receptacles also contain "mushroom hook" type hook and loop material for the purpose of adhering and detaching the housings to and from the receptacles. Additionally, the housings and receptacles have recessed areas for adhesion of the "mushroom hook" hook and loop material.

In another embodiment of the invention, the receptacle of the disposable bandage apparatus may be the mushroom hook material itself which may be attached directly to the adhesive strip for the selective engagement of the housings of the probe assembly.

Finally, and in the preferred embodiment of the invention, the light-emitting diode and photocell detector of the probe assembly may be mounted in modular housings with locking levers which can engage an indentation or slot in the receptacles and securely lock the housings into proper position within the receptacles, thus allowing the transmission and reception of infrared light through the mated housings and receptacles and through the appendage of a patient. In this embodiment, the silicone, or other radiation transparent windows, may be mounted against the skin of a patient, and may be used to secure the receptacles on the opposite side of the bandage strip. This is accomplished by the use of locking levers which are pushed through holes or slots in the bandage and engage the receptacles mounted on the opposite side of the bandage, thus sandwiching the bandage in between.

DESCRIPTION OF THE DRAWINGS

The above and other advantages of the invention will become more clear when considered with the following specification and accompanying drawings wherein.

DESCRIPTION OF THE REUSABLE PULSE OXIMETER SENSOR

Figure 1:
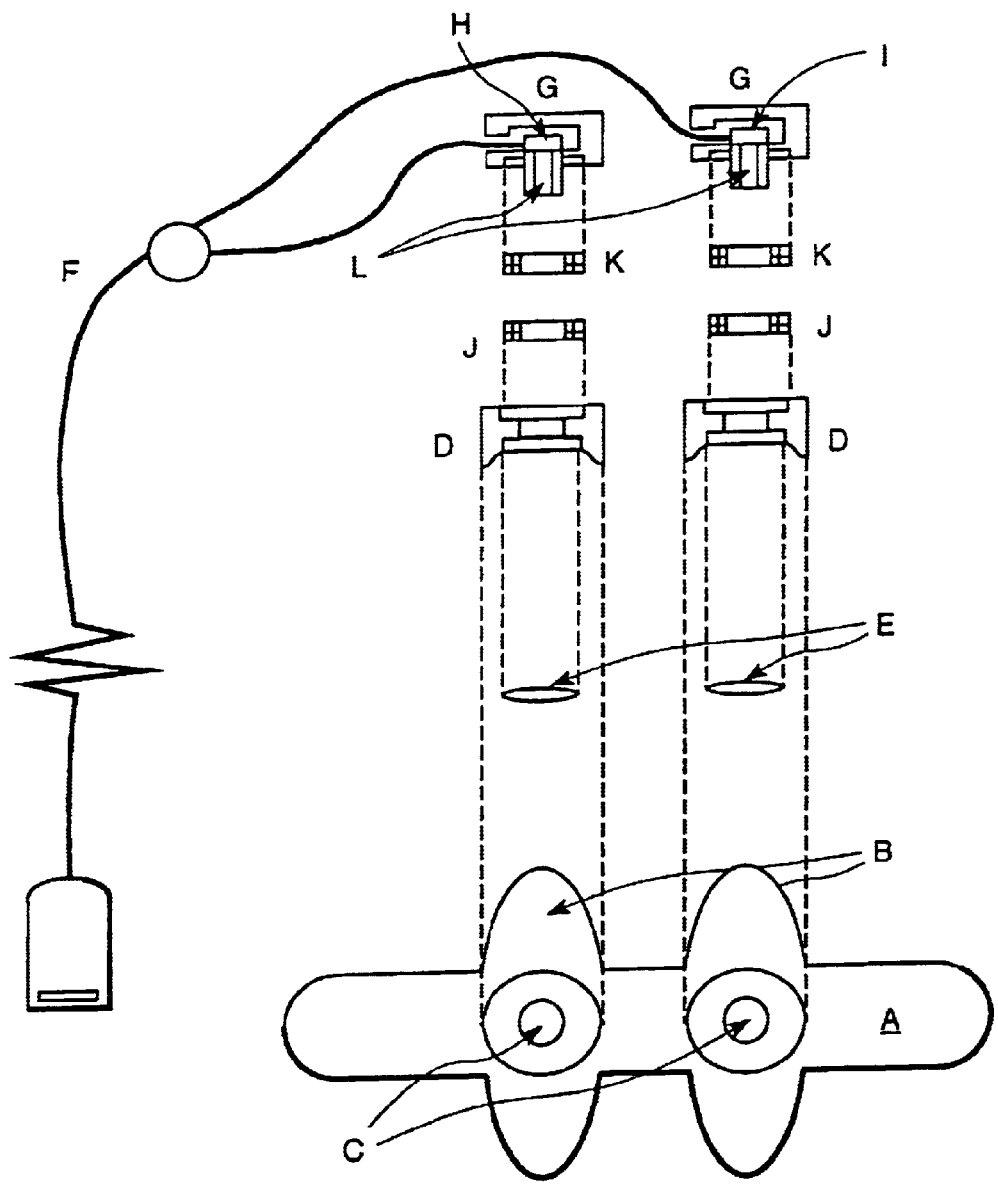
FIG. 1 is an exploded view of the reusable pulse oximeter probe and disposable bandage apparatus incorporating the invention.

The reusable pulse oximeter sensor constitutes a "Y" style pulse oximeter probe shown in FIG. 1, Item F. The probe incorporates two plastic housings shown as FIG. 1, Items G. The housings contain apertures or radiation transparent windows L therein. One housing contains the light-emitting diode of the probe, FIG. 1, Item H, and other contains the photocell detector, FIG. 1, Item I. The emitter and detectors are aligned with the apertures or windows L of the housings in order to transmit and receive light through a human appendage.

Seated within a recessed area of each housing, and attached permanently thereto, is a "mushroom hook" adhesive-backed pad, FIG. 1, Item K. The purpose of these pads is to selectively engage the "mushroom hook" pads, FIG. 1, Items J, attached permanently to the plastic discs, FIG. 1, Items D, and to attach the reusable probe assembly to the Disposable Bandage Apparatus. The reusable pulse oximeter sensor is shown assembled as FIG. 2, Item A.

Figure 5:
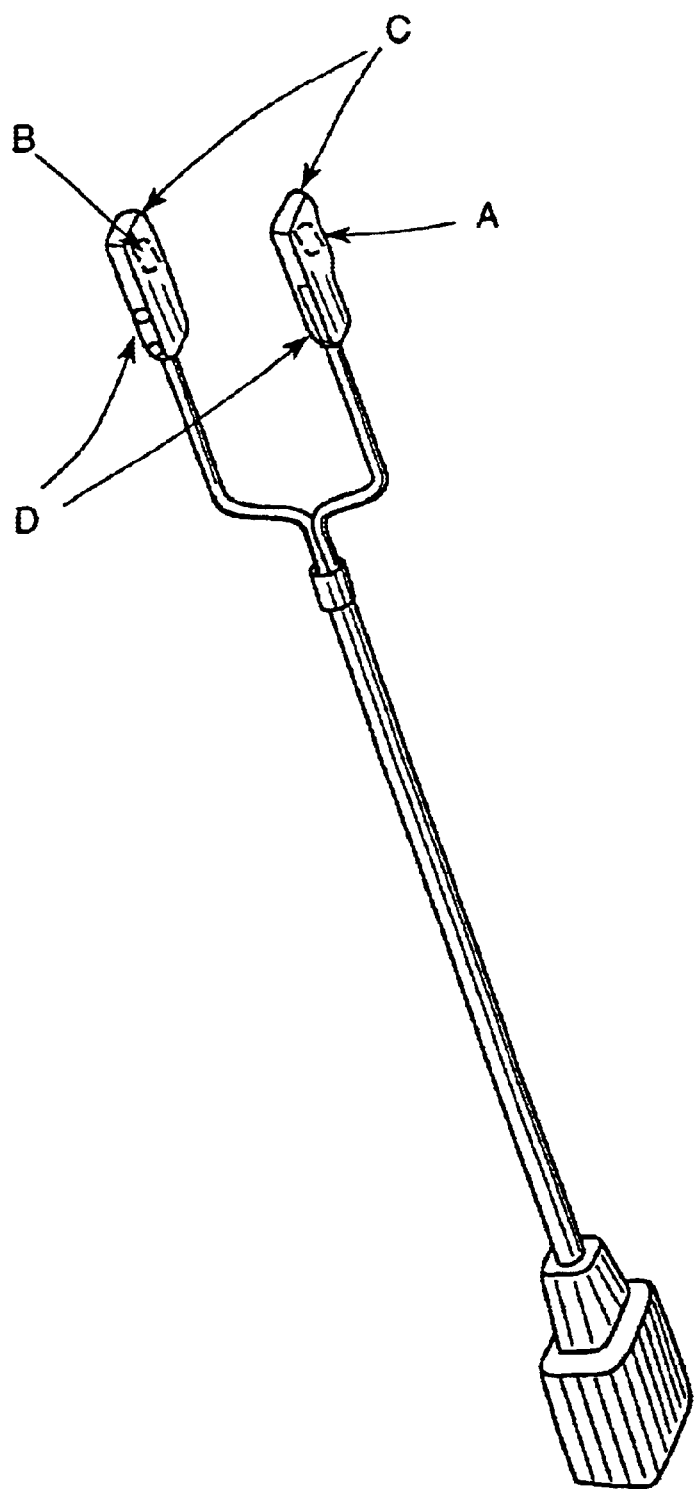
FIG. 5 illustrates an assembled view of the preferred embodiment of the reusable pulse oximeter sensor in which the light-emitting diode and photocell detector of the reusable probe are mounted in modular housings with locking levers.
Figure 6:
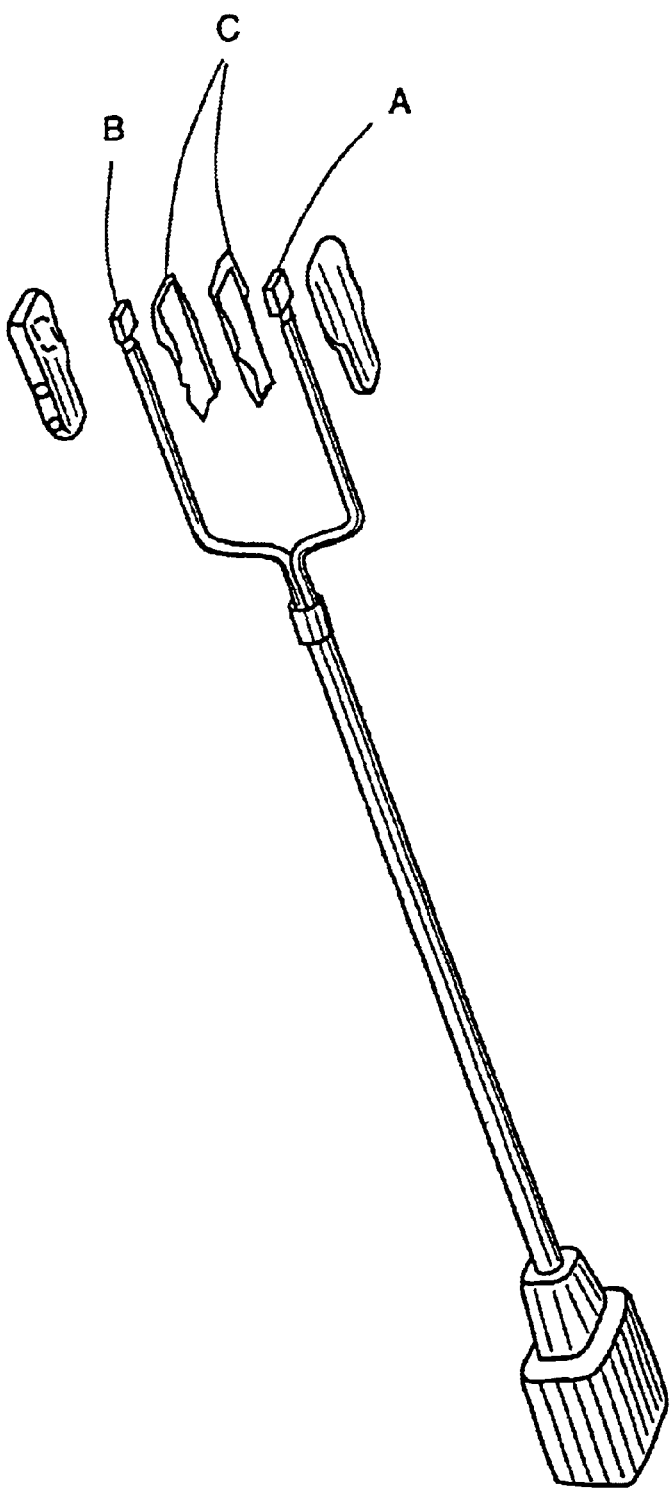
FIG. 6 illustrates an exploded view of the preferred embodiment of the reusable pulse oximeter sensor.

In the preferred embodiment of the reusable pulse oximeter sensor, the light-emitting diode (FIG. 5, Item A) and photocell detector (FIG. 5, Item B) of the probe assembly are housed in modular receptacles (FIG. 5, Items C) having locking levers (FIG. 5, Items D) for engaging the receptacles of the disposable bandage apparatus, and locking them into place. In this embodiment, the light-emitting diode (FIG. 6, Item A) and the photocell detector (FIG. 6, Item B) are sandwiched between interlocking receptacle halves, the bottom halves of which (FIG. 6, Items C) are made of a radiation transparent material. According to the present invention, intra-departmental or inter-institutional transport is greatly facilitated by having a bandage device which will accept probes of various manufacturers, as long as those probes contain housings that will matedly engage the receptacles of the disposable bandage apparatus.

Description of the Disposable Bandage Apparatus

The components of the apparatus include an adhesive-backed strip, shown as FIG. 1, Item A, the strip A incorporating two oval protrusions B centered thereon and shown as FIG. 1. The strip also incorporates two apertures, centrally located within the oval protrusions, each aperture C having a diameter sufficient in size to accommodate the transmission and reception of light from a light-emitting diode and photocell detector of a pulse oximeter probe.

On top of the apertures C are seated two plastic discs, FIG. 1, Item D, each having a concave base designed to conform to the radius of a human digit, and an aperture of slightly larger diameter than the apertures in the adhesive backed planar strip. The plastic discs are affixed to the adhesive planar strip by means of a permanent adhesive.

Seated in a recessed area on top of each plastic disc is a "mushroom hook", adhesive backed pad shown as FIG. 1, Item J. The purpose of the "mushroom hook" pads is to selectively engage the "mushroom hook" pads attached to the probe, FIG. 1, Items K, and to attach the probe to the disposable bandage apparatus. Sandwiched between the two plastic discs and the planar adhesive strip are two translucent silicone windows, FIG. 1, Item E. The windows are designed to permit the passage of infrared light and yet prevent contact between probe and patient, and consequently, contamination of the reusable probe itself.

Figure 2:
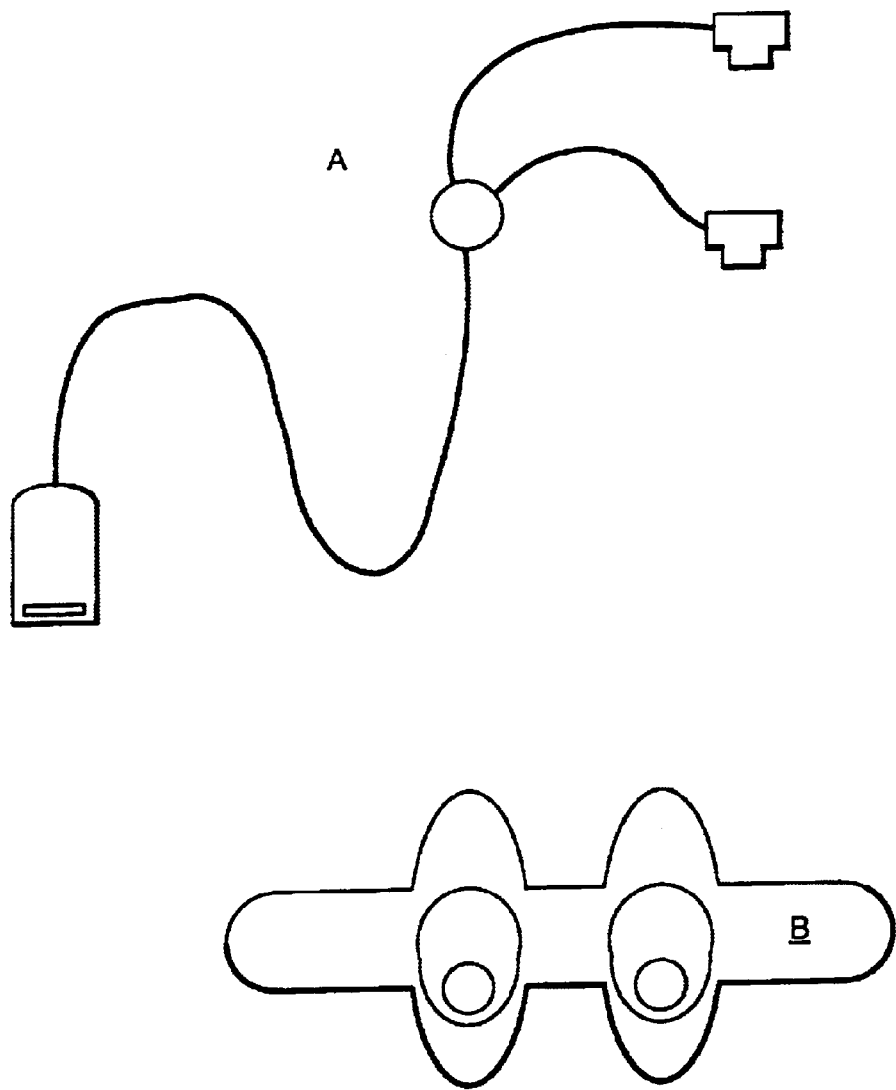
FIG. 2 is a view of the reusable pulse oximeter probe and disposable bandage apparatus shown individually as components of the invention.

The above items constitute the disposable bandage apparatus of the invention, the apparatus being shown assembled as FIG. 2, Item B.

Figure 4:
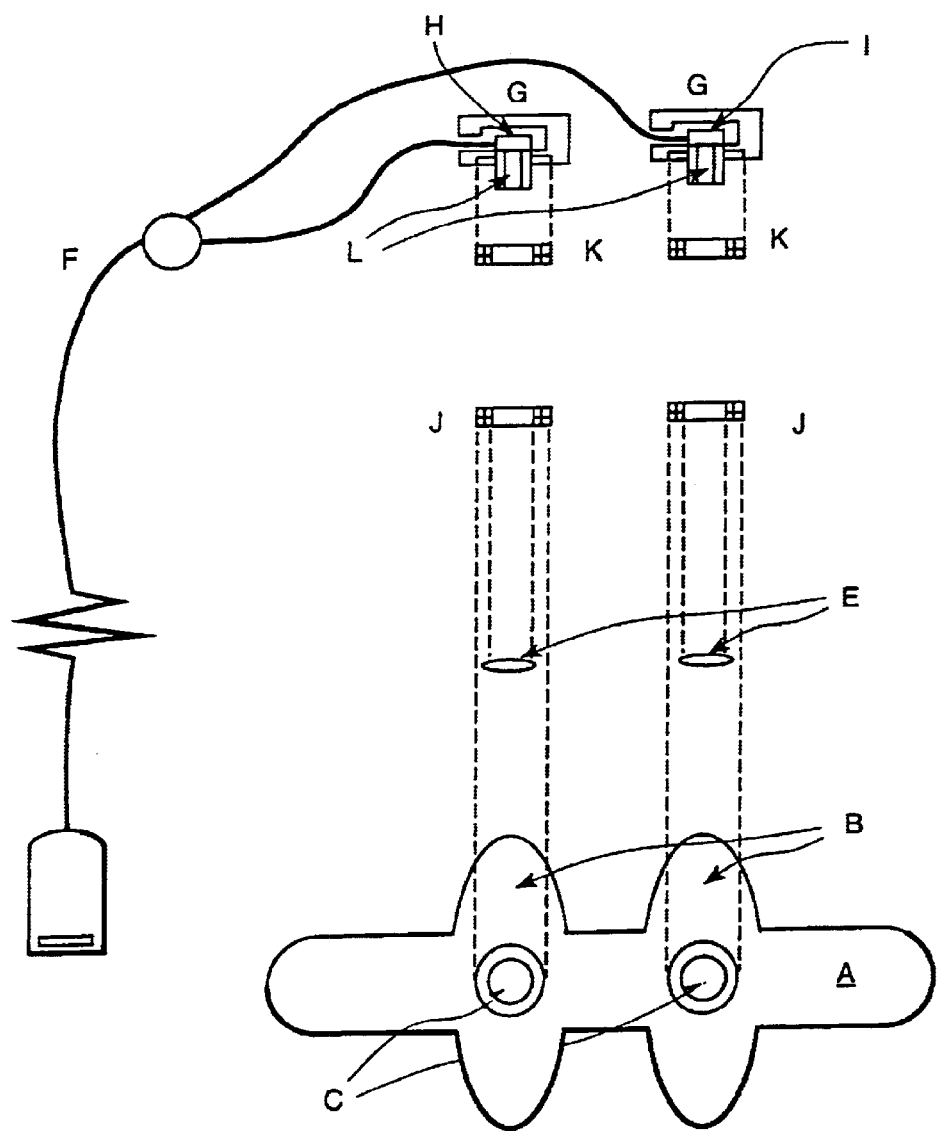
FIG. 4 illustrates an exploded view of another embodiment of the invention in which the "mushroom hook" material itself is used as the receptacle of the disposable bandage apparatus.

In another embodiment of the invention, the disposable bandage apparatus may be configured as in FIG. 4 of the drawings. FIG. 4 is an exploded view of the apparatus in which the "mushroom hook" pads of the bandage apparatus, FIG. 4, Items J, are bonded directly to the adhesive planar strip, FIG. 4, Item A, for the selective engagement of the "mushroom hook" pads of the probe, FIG. 4, Items K, the pads being attached permanently to the housings of the probe, FIG. 4, Items G.

Figure 7:
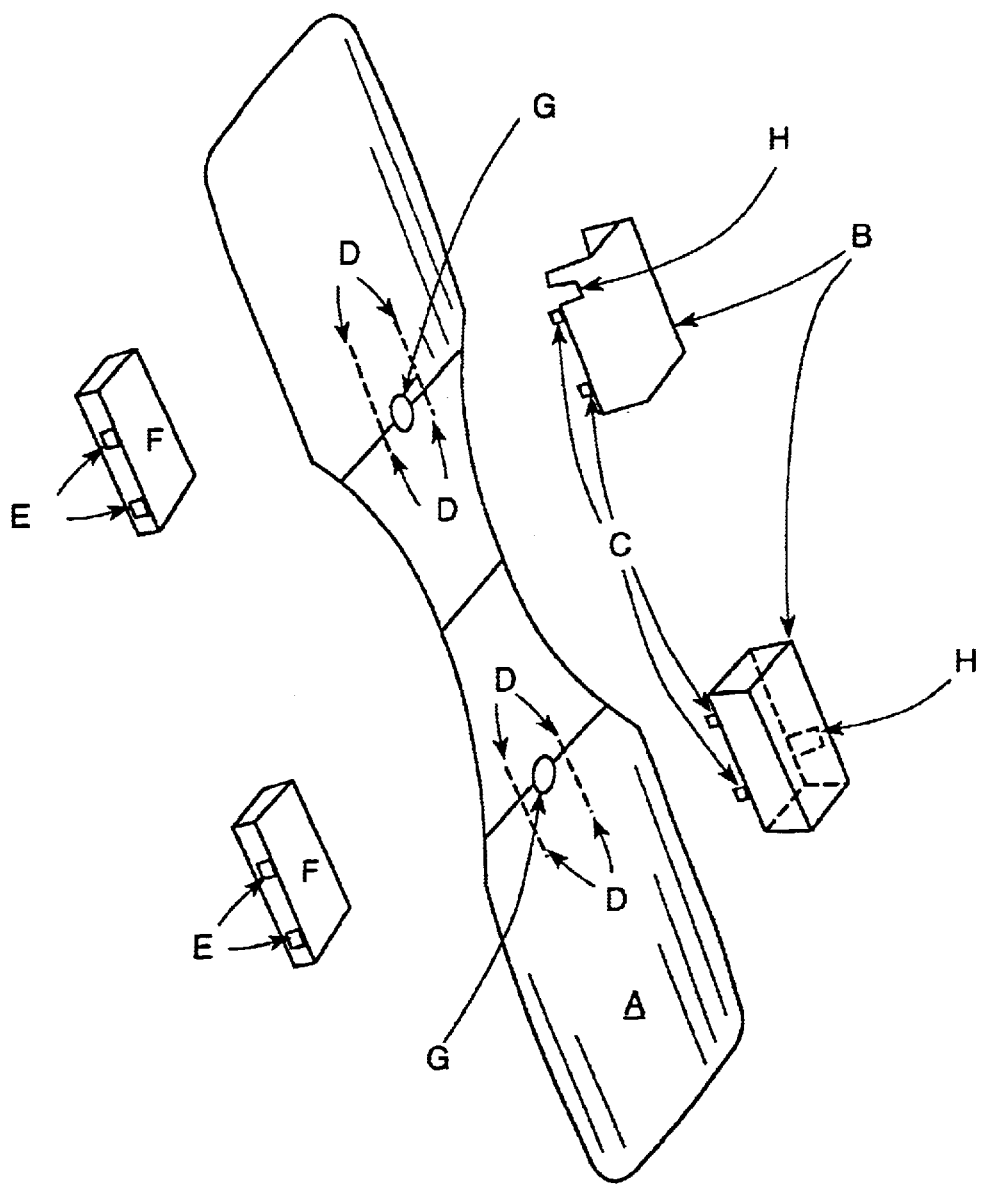
FIG. 7 illustrates an exploded view of the preferred embodiment of the bandage apparatus in which the receptacle tops incorporate a slot for engaging the locking levers of the modular probe housings, and wherein the radiation transparent windows are mounted on the opposite side of the bandage strip thus sandwiching and securing the bandage in between the two receptacle halves by means of locking levers.
Figure 8:
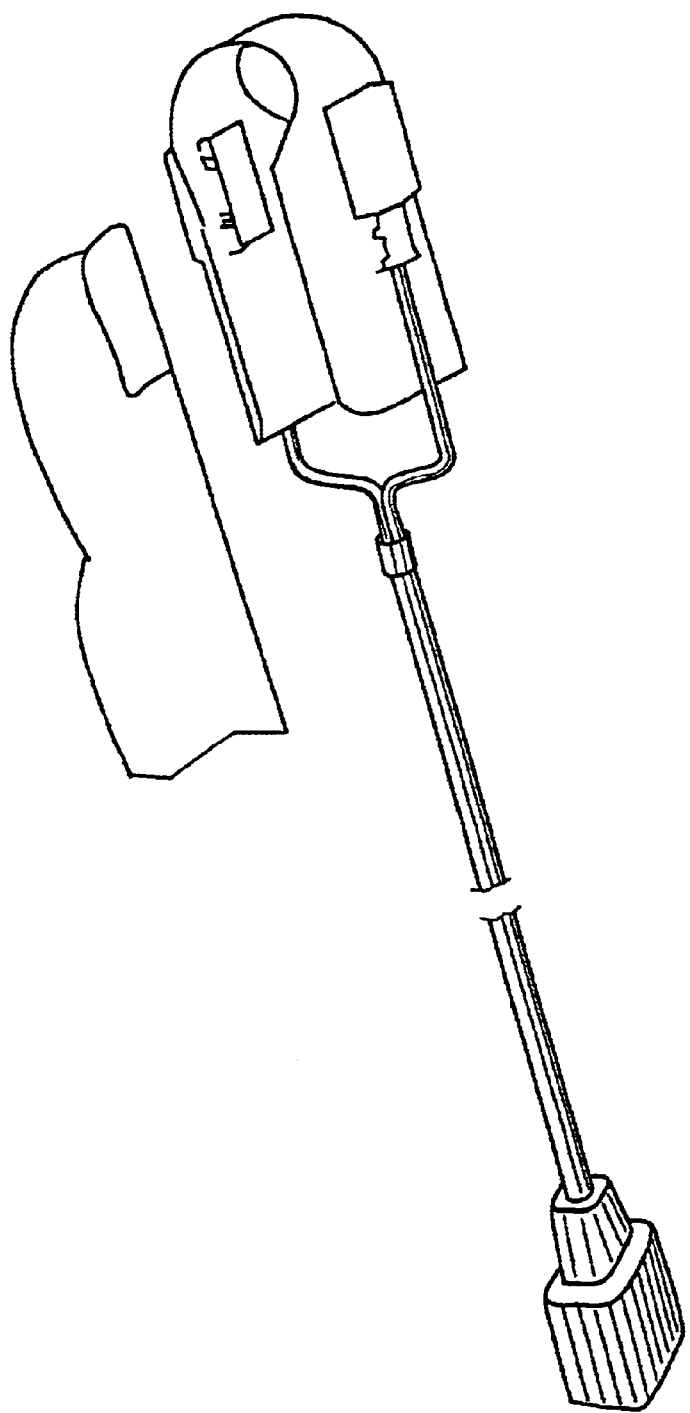
FIG. 8 illustrates the preferred embodiment of the invention as it would appear ready for use on a human digit.

In the preferred embodiment of the disposable bandage apparatus, the bandage strip (FIG. 7, Item A) is sandwiched between interlocking receptacle halves. The top halves of the receptacles (FIG. 7, Items B) contain locking levers (FIG. 7, Items C) that are pushed through slots cut in the bandage strip (FIG. 7, Items D) and lockingly engage indentations (FIG. 7, Items E) in the bottom halves of the receptacles (FIG. 7, Items F), thus sandwiching and locking the bandage in between. The bandage strip contains two apertures (FIG. 7, Items G) for the transmission and reception of light from the light-emitting diode and photocell detector of the pulse oximeter sensor which are encased in modular housings having locking levers (FIG. 5, Items D) wherein the levers engage slots in the receptacles (FIG. 7, Items H) thereby locking the housings into place within the receptacles. In addition, the bottom halves of the receptacles (FIG. 7, Items F) are of a radiation transparent material, thus allowing the light-emitting diode and photocell detector contained in the probe housings, when engaged in the bandage receptacles, to transmit and receive light through the apertures of the bandage strip and through the radiation transparent material of the bottom halves of the receptacles, and through the appendage of a patient. The complete reusable pulse oximeter probe and bandage assembly is shown assembled and ready for use on a human digit in FIG. 8.

Other Fastening Means

As can be appreciated, there are many ways of fabricating the above components of the invention. The above description describes attachment of the reusable pulse oximeter sensor to the disposable bandage apparatus by way of a "mushroom hook" type hook and loop material and by the use of telephone type modular connectors and receptacles. In addition to this means, a number of other methods may be used including standard hook and loop material, "ring and groove" type snap-on connectors, "push and twist" type Luerlock connectors, and threaded flange type connectors.

Method of Use

Figure 3:
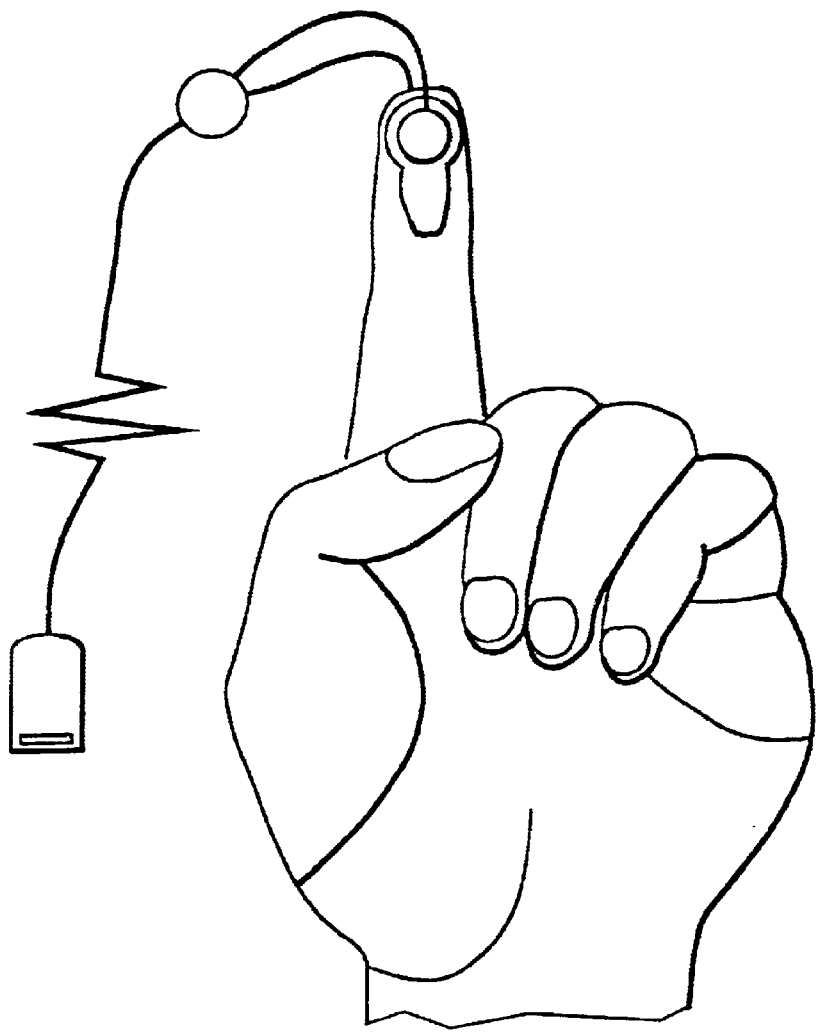
FIG. 3 illustrates the invention in use on a human finger or digit.

For use on each individual patient, the probe is affixed in the following manner:

Firstly, the backing is removed from the adhesive strip of the disposable bandage apparatus. One of the apertures of the apparatus is visually positioned on the center of the nail bed of the patient's appendage and one side of the adhesive strip and the oval protrusions are adhered to the patient's digit. The rest of the strip is then looped over the end of the patient's appendage, and the plastic disc is aligned so as to exactly oppose the plastic disc already attached to the other side of the digit. Once the disposable bandage apparatus has been properly adhered to the patient, the plastic housings of the probe assembly can be easily snapped into place on opposing sides of the digit. The entire assembled probe is shown as it would appear in use on a patient in FIG. 3.

For use with each patient, the modular probe and bandage assembly, which is the preferred embodiment of the invention, would be attached as follows:

Firstly, the backing is removed from the adhesive strip. The strip is then folded where indicated on the bandage and the strip is then adhered to opposing sides of the human digit. Once the bandage apparatus is in place, the housings of the probe are pushed into the receptacles and locked in place by means of the locking levers. When the patient is moved between different service areas of a hospital, the probes can be removed and the patient transported to a new service area where that area's oximeter probes are pushed into the receptacles for further oximeter readings.

Figure 9:
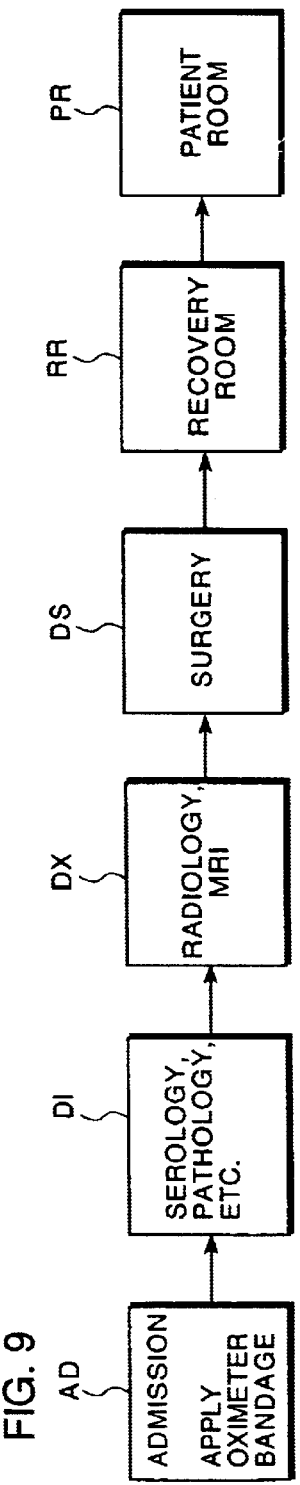
FIG. 9 is a patient flow diagram showing the intra-departmental or inter-institutional transport of a patient.

As shown in FIG. 9, the invention is easily adaptable to different manufacturers' oximeters being used in different departments or institutions when the patient is to be transported between the departments or institutions. As shown in FIG. 9, at the admissions area AD, when the patient is admitted to the hospital or facility, an oximeter bandage is initially applied. Then the patient may go through another testing area or department D1 where various serological, pathological tests may be run. Then the patient is shown as being transported to a radiology area such as where X-ray and magnetic resonance images (MRI) scans are made. Other departments may have the patient transported thereto such as a surgery department DS and a recovery room RR and the patient's room PR where, in each instance, a different manufacturer or different oximeter probes may be attached where, according to the invention, the receptacles on the bandages are able to receive and retain housings on the emitter and detector elements of the probe.

Figure 10:
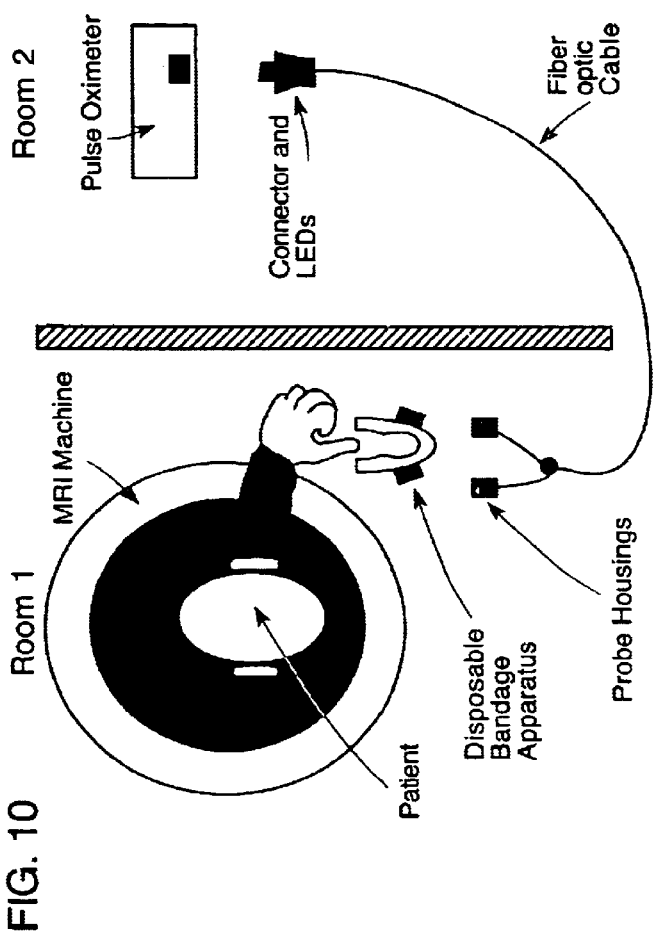
FIG. 10 is a schematic illustration of how the probe housings can utilize fiberoptic cable connecting the light emitter and detector to the disposable bandage according to the invention.

An example of the flexibility of the system of this invention is illustrated in FIG. 10. In this pictorial embodiment, a magnetic resonance image system or an MRI machine is shown as being positioned in one room with the patient and having applicant's disposable bandage apparatus attached to the finger of a patient. In this case, the patient is in the MRI facility where the patient is just having MRI work done. The probe housings are shown attached at the ends of fiberoptic cable connected to a connector which has the light-emitting diode and the light detector incorporated therein with a connector or plug for plugging into a pulse oximeter PO. The light-emitting and light-receiving ends of the fiberoptic cable are directed or oriented in the modular housings to emit IR light into the finger and receive IR light transmitted through the finger. It will be noted that since in the MRI application no ferrous materials are allowed, the LED's are placed in a room many feet away (up to fifty or more feet away) and (the oximeter device is in optical communication with the applicant's bandage apparatus. Thus, in situations where non-ferrous materials are required, the probe has non-ferrous housings and materials designed to matedly engage with the receptacles of applicant's disposable bandage apparatus. The housings of the probe are in fiberoptic communication with the LED's which would be at the other end of the probe near the pulse oximeter.

As shown above, in case of magnetic resonance imaging (MRI) situations where the presence of any metal in the environment can effect the MRI readings, the probe and emitter elements are situated remotely from the MRI machine and fiberoptic cable conveys light to and from the patient's finger. In this case, the oximeter probe housings are the termination ends of the fiberoptic cable and the modular housings are therefore able to be inserted into the bandage receptacles and the oximeter readings taken in this fashion from a remote area.

In all embodiments of the invention, when the probe is no longer required on the patient, the housings of the reusable probe are simply unsnapped from the disposable bandage apparatus, the bandage apparatus is thrown away, and the probe can then be reused on a new patient in conjunction with a new bandage apparatus.

Advantages of the Present Invention

Intra-departmental or inter-institutional transport is greatly facilitated by having a bandage device which will accept probes of various manufacturers, as long as those probes contain housings that will matedly engage the receptacles of the disposable bandage apparatus.

Current reusable pulse oximeter probes are either "clam shell" type clamping devices which can restrict circuit or "Y" type probes which are taped directly to the patient. Both types also come in direct contact with the patient's skin and bodily fluids and need sterilization after use. Because of the fact that these devices incorporate many surfaces and at times, porous materials, proper sterilization is very difficult. With the present invention there is no contact between the reusable probe and the skin or bodily fluids of the patient.

Disposable probes are very costly because of the fact that the cable, connectors and photodiodes are all disposed of after use. The present invention accomplishes the same goals as a disposable probe from a cleanliness standpoint, but since only the attachment apparatus is discarded after use, the cost is much less to a healthcare institution.

With the concave shape of the plastic discs of the bandage apparatus, when backed by the adhesive strip, the device is extremely effective in preventing the entrance of extraneous light from the sides of the patient's digit. Current probes on the market, whether disposable or reusable, because of the nature of their shape and affixation means, have problems in dealing with extraneous light reception.

The present invention is facilitated by easy snap-on, snap-off, or modular connector attachment means for attaching the probe to the disposable bandage apparatus. Probe-shield type devices available in the past not only required the modification of the original manufacturer's probe, but required the difficult procedure of inserting a flexible laminated probe into a sheath for each patient.

Probe-shield devices, because of the lamination process involved, raised some concern over the transmission and reception of infrared light through the laminating material. The present invention uses a silicone window for the isolation of the probe from the patient. Infrared light transmission and reception is not affected by passage through translucent silicone.

In these days of environmental consciousness, the annual waste generated from tens of millions of disposable probes is enormous. The present invention, if used in considerable numbers, would greatly reduce the amount of environmental waste generated by disposable pulse oximeter probes.

While the invention has been described in relation to preferred embodiments of the invention, it will be appreciated that other embodiments, adaptations and modifications of the invention will be apparent to those skilled in the art.

What is claimed is:

1. A method of facilitating the intra-departmental or inter-institutional transport of a patient requiring pulse oximeter monitoring, and wherein at each department and institution different pulse oximeters and oximeter probes are used for monitoring said patient, comprising:

affixing to said patient a bandage apparatus having a modular emitter receptacle and a modular detector receptacle incorporated thereon constituting an affixed disposable bandage apparatus, providing each said different pulse oximeter probe with a modular emitter housing and a modular detector housing adapted to matedly engage and/or disengage said emitter and detector receptacles, respectively, of an affixed disposable bandage apparatus, and connecting said modular emitter receptacle and said modular detector receptacle with a respective modular emitter housing and modular detector housing of different pulse oximeters at each department and/or institution without changing said affixed disposable bandage apparatus.

2. The method of facilitating the intra-departmental or inter-institutional transport of a patient requiring pulse oximeter monitoring as defined in claim 1, wherein one of said departmental or institutional points includes an MRI machine, and said method further comprises locating said pulse oximeter at some remote location from the MRI machine and said connecting step includes using fiberoptic cables to connect the light emitter and light detector, respectively, of said pulse oximeter to the bandage apparatus, further characterized in that said fiberoptic cables have a modular housing adapted to serve as a light emitter and a further modular housing adapted to serve as a light receiver for conveying light that has passed through said patient via said fiberoptic cables to a light detector at said pulse oximeter.

3. A method of facilitating the intra-departmental or inter-institutional transport of a patient requiring pulse oximeter monitoring, and wherein at each department and institution different pulse oximeters and oximeter probes are used for monitoring said patient, comprising:

affixing to said patient a bandage apparatus having a modular emitter receptacle and a modular detector receptacle incorporated thereon constituting an affixed disposable bandage apparatus, providing each said different pulse oximeter probe with a modular emitter housing and a modular detector housing adapted to matedly engage and/or disengage said emitter and detector receptacles, respectively, of an affixed disposable bandage apparatus, and connecting said modular emitter receptacle and said modular detector receptacle with a respective modular emitter housing and modular detector housing of different pulse oximeters at each department and/or institution without removing said affixed disposable bandage apparatus.

* * * * *